US012779133B2

(12) United States Patent
Carlsson

(10) Patent No.: US 12,779,133 B2
(45) Date of Patent: Nov. 3, 2026

(54) SUB-ASSEMBLY FOR A MEDICAMENT DELIVERY DEVICE

(71) Applicant: SHL Medical AG, Zug (CH)

(72) Inventor: Daniel Carlsson, Nacka Strand (SE)

(73) Assignee: SHL Medical AG, Zug (CH)

( * ) Notice: Subject to any disclaimer, the term of this patent is extended or adjusted under 35 U.S.C. 154(b) by 335 days.

(21) Appl. No.: 18/709,908

(22) PCT Filed: Nov. 3, 2022

(86) PCT No.: PCT/EP2022/080674
§ 371 (c)(1),
(2) Date: May 14, 2024

(87) PCT Pub. No.: WO2023/088686
PCT Pub. Date: May 25, 2023

(65) Prior Publication Data
US 2025/0001093 A1 Jan. 2, 2025

(30) Foreign Application Priority Data
Nov. 17, 2021 (EP) .................................... 21208664

(51) Int. Cl.
*A61M 5/32* (2006.01)
*A61M 5/31* (2006.01)

(52) U.S. Cl.
CPC ........ *A61M 5/3204* (2013.01); *A61M 5/3134* (2013.01)

(58) Field of Classification Search
CPC .......................... A61M 5/3204; A61M 5/3134
(Continued)

(56) References Cited

U.S. PATENT DOCUMENTS

2017/0354789 A1* 12/2017 Bendek ................. A61F 9/0008
2019/0022320 A1* 1/2019 Carlsson ............. A61M 5/2033

FOREIGN PATENT DOCUMENTS

EP 3257540 A1 12/2017
FR 3039068 B1 1/2017
(Continued)

OTHER PUBLICATIONS

International Search Report and Written Opinion for corresponding PCT application No. PCT/EP2022/080674 dated Feb. 20, 2023.

*Primary Examiner* — Phillip A Gray
(74) *Attorney, Agent, or Firm* — McDonnell Boehnen Hulbert & Berghoff LLP

(57) ABSTRACT

The present disclosure provides a sub-assembly for a medicament delivery device. The sub-assembly includes a cap comprising an outer cap body, and a needle shield remover having a tubular inner cap body arranged concentrically with and radially inwards of the outer cap body. The tubular inner cap body defines a central channel configured to receive a needle shield. The needle shield remover includes a gripping arm extending axially in a distal direction from a distal tubular inner cap body end of the tubular inner cap body. The sub-assembly further includes a medicament container holder comprising a holding body configured to receive a medicament container, the holding body having a proximal holding body end provided with a c-clip structure, the c-clip structure having open ends in the circumferential direction of the holding body. An axial slot is formed between the open ends. The c-clip structure has a radially inwards extending ledge configured to axially support a shoulder of the medicament container, and the gripping arm is configured to be arranged in the slot and engage with a distal end face of the needle shield.

14 Claims, 4 Drawing Sheets

(58) Field of Classification Search
USPC ........................................................... 604/19
See application file for complete search history.

(56) References Cited

FOREIGN PATENT DOCUMENTS

| | | | | | |
|---|---|---|---|---|---|
| GB | 2438593 | A | * | 12/2007 | .......... A61M 5/3202 |
| WO | 2007138299 | A1 | | 12/2007 | |

* cited by examiner

SUB-ASSEMBLY FOR A MEDICAMENT DELIVERY DEVICE

CROSS-REFERENCE TO RELATED APPLICATIONS

The present application is a U.S. National Phase Application pursuant to 35 U.S.C. § 371 of International Application No. PCT/EP2022/080674 filed Nov. 3, 2022, which claims priority to European Patent Application No. 21208664.9 filed Nov. 17, 2021. The entire disclosure contents of these applications are herewith incorporated by reference into the present application.

TECHNICAL FIELD

The present disclosure generally relates to medicament delivery devices.

BACKGROUND

Medicament delivery devices such as autoinjectors may accommodate a syringe provided with a needle. A medicament delivery device of this type may comprise a needle shield that protects the needle and seals the syringe to ensure sterility of both the needle and the drug contained in the syringe. Such medicament delivery devices may have a cap that covers the needle shield. The cap may comprise a needle shield remover in the form of a sleeve arranged around the needle shield and provided with radially inwards extending tabs configured to engage with a peripheral surface of the needle shield when the cap is pulled off.

SUMMARY

There is hence according to a first aspect of the present disclosure provided a sub-assembly for a medicament delivery device, comprising: a cap comprising: an outer cap body, a needle shield remover having a tubular inner cap body arranged concentrically with and radially inwards of the outer cap body, the tubular inner cap body defining a central channel configured to receive a needle shield, the needle shield remover comprising a gripping arm extending axially in a distal direction from a distal tubular inner cap body end of the tubular inner cap body, a medicament container holder comprising: a holding body configured to receive a medicament container, the holding body having a proximal holding body end provided with a c-clip structure, the c-clip structure having open ends in the circumferential direction of the holding body, whereby an axial slot is formed between the open ends, wherein the c-clip structure has a radially inwards extending ledge configured to axially support a shoulder of the medicament container, wherein the gripping arm is configured to be arranged in the slot and engage with a distal end face of the needle shield.

The needle shield can thus be removed by means of a needle shield contained in a medicament delivery device when the cap is removed. Since the gripping arm engages with the distal end face of the needle shield instead of gripping into the peripheral surface, the material of which the needle shield remover is made does not have to be as durable as in the prior art, where the sleeve and tabs typically are made of steel. Thus, a higher flexibility of the design and potentially lower cost can be obtained.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device.

When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", or "circumferentially" refer to a circumference or a circumferential direction relative to an axis, typically a central axis extending in the direction of the longest extension of the device and/or component.

Similarly, "radial" or "radially" refer to a direction extending radially relative to the axis, and "rotation", "rotational" and "rotationally" refer to rotation relative to the axis.

According to one embodiment the outer cap body has a distal outer cap body end, and wherein the tubular inner cap body extends distally beyond the distal outer cap body end.

According to one embodiment the gripping arm comprises a radially inwards extending structure provided with a proximally directed radial surface configured to bear against the distal end face of the needle shield.

According to one embodiment the radially inwards extending structure has a gradually decreasing radial dimension in a direction towards a distal end face of the gripping arm.

According to one embodiment the cap is made of plastic.

The gripping arm may be made of plastic. The gripping arm may comprise or consist of plastic.

The needle shield remover may be made of plastic. The needle shield remover may comprise or consist of plastic.

According to one embodiment the central channel is dimensioned to tightly fit the needle shield.

According to one embodiment the central channel is dimensioned to accommodate a majority of the length of the needle shield.

According to one embodiment the central channel is dimensioned to accommodate at least 70% or 80% of the length of the needle shield.

According to one embodiment the distal tubular inner cap body end is arranged adjacent to the proximal holding body end.

According to one embodiment the needle shield remover comprises only one gripping arm.

According to one embodiment needle shield comprises a rigid needle shield, RNS, and/or a flexible needle shield, FNS.

One embodiment comprises a housing, wherein the housing is configured to receive the medicament container holder, wherein the housing has an inner wall arranged axially aligned with the c-clip structure, the inner wall being configured to restrict radial outward flexing of the c-clip structure.

According to one embodiment the inner wall comprises an axial inner wall slot configured to receive the gripping arm.

There is according to a second aspect of the present disclosure provided a medicament delivery device comprising a sub-assembly as claimed in any of the preceding claims.

Generally, all terms used in the claims are to be interpreted according to their ordinary meaning in the technical field, unless explicitly defined otherwise herein. All references to "a/an/the member, apparatus, component, means, etc." are to be interpreted openly as referring to at least one instance of the member, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which:

FIG. 6 is a longitudinal section of the medicament delivery device with the cap on.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like members throughout the description.

The present disclosure concerns a sub-assembly for a medicament delivery device. The medicament delivery device may for example be an autoinjector or a manual injector.

The sub-assembly includes a cap comprising a needle shield remover provided with a gripping arm, and a medicament container holder that has a c-clip structure having open ends between which an axial slot is formed.

The medicament container holder is configured to hold or accommodate a medicament container such as a syringe. The medicament container is provided with a needle and a needle shield arranged around the needle.

The gripping arm is configured to extend into the axial slot to thereby bear against a distal end face of the needle shield.

Medicament delivery devices that can comprise the herein described sub-assembly may have a power pack assembly which is configured to perform the dispensing of a drug contained in the medicament container.

The power pack assembly may for example comprise a spring-loaded plunger rod or a gas-driven plunger rod. For illustrative purposes, the example of a medicament delivery device comprising the sub-assembly disclosed in the following comprises a spring-loaded plunger rod.

Figure 1:
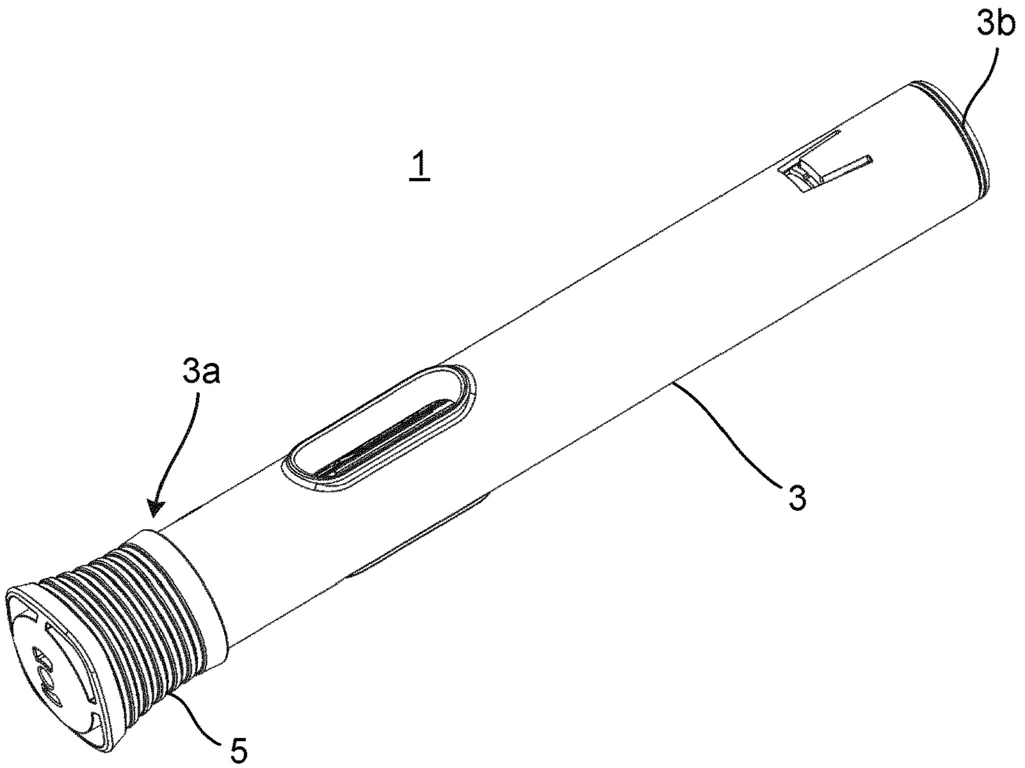
FIG. 1 is a perspective view of an example of a medicament delivery device comprising an example of sub-assembly according to the present disclosure.

Turning now to FIG. 1 an example of a medicament delivery device 1 is shown. The medicament delivery device 1 is an autoinjector.

The medicament delivery device 1 comprises a housing 3. The housing 3 has a proximal end 3*a* and a distal end 3*b*. The housing 3 is hollow and may be generally tubular. The housing 3 may comprise a proximal end opening.

The medicament delivery device 1 comprises a cap 5. The cap 5 can be fitted to the proximal end 3*a* of the housing 3 and/or onto a delivery member cover (not shown in FIG. 1) protruding from the proximal end opening of the housing 3.

Figure 2:
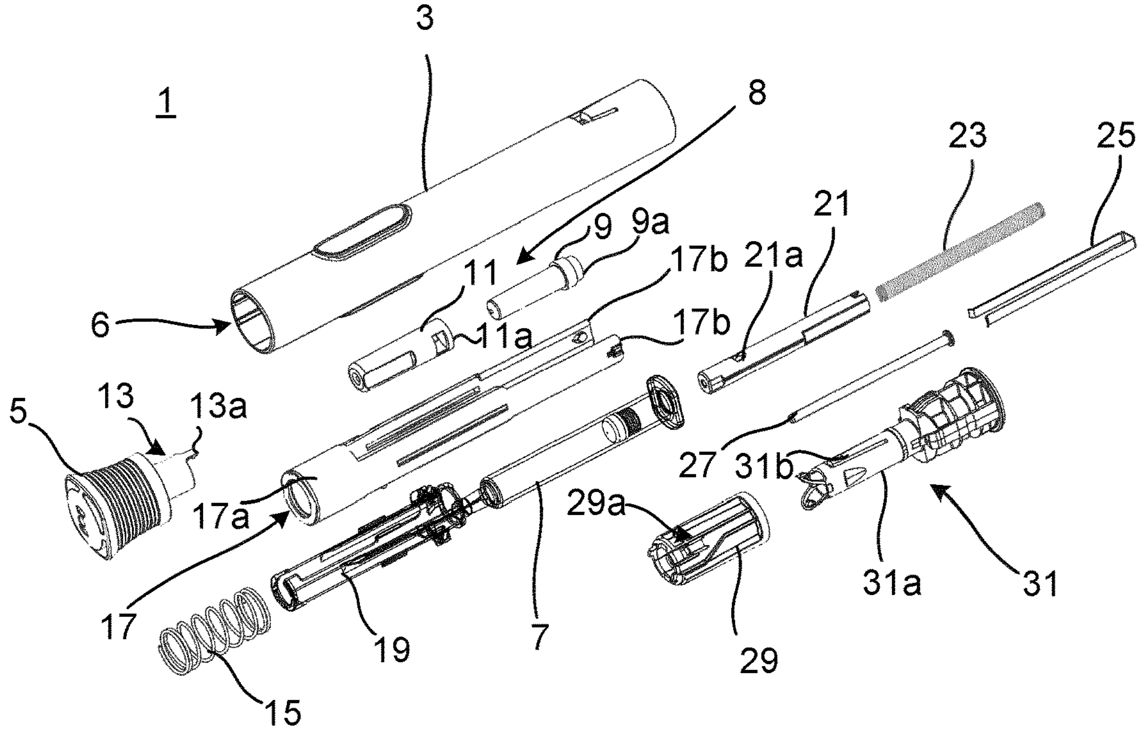
FIG. 2 shows an exploded view of the medicament delivery device in FIG. 1

FIG. 2 is an exploded view of the medicament delivery device 1.

The medicament delivery device 1 is configured to accommodate a medicament container 7 such as a syringe. The medicament container holder 7 comprises a delivery member, e.g., a needle.

The delivery member is fitted with a needle shield 8. The needle shield 8 may comprise a flexible needle shield (FNS) 9 and/or a rigid needle shield (RNS) 11. In an example where the needle is fitted the needle shield 8 comprising both the FNS 9 and the RNS 11, the RNS 11 may be arranged around the FNS 9.

The cap 5 comprises a needle shield remover 13 configured to engage with the needle shield 8.

The needle shield remover 13 comprises an axially extending gripping arm 13*a*. The gripping arm 13*a* extends in the distal direction. The gripping arm 13*a* is configured to bear against or engage with a distal end face of the needle shield 8. The distal end face may be the distal end face 11*a* of the RNS 11 and/or the distal end face 9*a* of the FNS 9.

When the cap 5 is removed, it brings with it the needle shield 8, e.g., the RNS 11 and the FNS 9. In one preferred example, the cap comprises a retaining section arranged inside the needle shield remover. The retaining section is configured to hold the needle shield, so that the needle shield will not fall off from the proximal end of the cap. Alternatively, the cap comprises a closed proximal end. In one example where the cap comprises a retaining section, the retaining section is preferably arranged at the proximal end of the needle shield remover. For example, the retaining section is an annular ledge extending from an inner surface of the needle shield remover. Alternatively, the retaining section is one or more axially extending ribs arranged on the inner surface of the needle shield remover.

The medicament delivery device comprises the aforementioned delivery member cover 17. The delivery member cover 17 is slidably arranged in the housing 3 and extends from the proximal end opening 6 of the housing 3.

The delivery member cover 17 is configured to move axially relative to the housing 3 from an extended position to a retracted position in which the housing 3 receives a larger portion of the delivery member cover 17 than in the extended position.

The delivery member cover 17 is biased towards the extended position. The medicament delivery device 1 comprises a first resilient member 15 configured to bias the delivery member cover 17 towards the extended position. The first resilient member 15 may for example be a coil spring.

The first resilient member 15 may for example be arranged to extend inside the delivery member cover 17 between a radial surface of the delivery member cover 17 and a radial surface provided inside the housing 3.

The delivery member cover 17 has a proximal tubular portion 17*a* and legs 17*b* extending distally towards the distal end 3*b* of the housing 3.

The medicament delivery device 1 comprises a medicament container holder 19. The medicament container holder 19 is arranged in the housing 3 and is configured to hold a medicament container such as the syringe 7.

The housing 3 may for example comprise a radially inwards extending ledge which prevents the medicament container holder 19 from moving in the proximal direction, i.e., towards the proximal end 3*a* of the housing 3.

The medicament delivery device 1 comprises a plunger rod 21. The plunger rod 21 is configured to extend into the medicament container, i.e., the syringe 7 in this example.

The plunger rod 21 is configured to move in the proximal direction inside the housing 3. The plunger rod 21 is configured to be moved from an initial axial position to a final position, which is closer to the proximal end 3*a* of the housing 3 than the initial axial position.

The plunger rod 21 comprises radial recesses 21*a*. Alternatively, the plunger rod may comprise a ledge extending from an outer surface of a wall of the plunger rod in the radial direction.

The plunger rod 21 may be hollow, as in the example in FIG. 2. Alternatively, the plunger rod may comprise a tubular section and a rod section.

The exemplified medicament delivery device 1 comprises a rod 27 and a second resilient member 23. The rod 27 is configured to be arranged in the plunger rod 21 and the second resilient member 23, for example a spring, may be arranged around the rod 27. Alternatively, the second resilient member 23 may be arranged partially around the plunger rod, in which case the medicament delivery device is without the rod 27.

In one example, the medicament delivery device comprises a gas canister and a valve connected to the gas canister for driving the plunger rod from the initial axial position instead of the second resilient member.

The medicament delivery device 1 may comprise a U-shaped bracket 25. The U-shaped bracket 25 is arranged with its bottom of the U-shape facing towards the distal end 3*b* of the housing 3. The second resilient member 23 is configured to bias the U-shaped bracket 25 towards the distal end 3*b* of the housing 3.

The medicament delivery device 1 comprises a rotator 29 and a rear cap structure 31.

The rear cap structure 31 is configured to engage with the plunger rod 21 to maintain the plunger rod 21 in its initial axial position. The rear cap structure 31 has a tubular proximal portion 31*a* provided with radially flexible arms 31*b*. Each flexible arm 31*b* is configured to engage with a respective radial recess 21*a* of the plunger rod 21 before the medicament delivery device 1 has been activated or triggered to perform medicament delivery.

The rotator 29 is arranged radially outside of and around the tubular proximal portion 31*a*. The rotator 29 is configured to rotate relative to the tubular proximal portion 31*a* from a first rotational position, which it holds prior to activation of the medicament delivery device 1, to a second rotational position.

The rotator 29 has an inner surface which when the rotator 29 is in the first rotational position bears against the flexile arms 31*b*, preventing the flexible arms 31*b* to disengage from a respective one of the radial recesses 21*a*.

The rotator 29 has an inner surface provided with inner recesses or windows which are arranged circumferentially offset from the flexible arms 31*b* when the rotator 29 is in the first rotational position.

The rotator 29 is configured to cooperate with the delivery member cover 17 when the delivery member cover 17 is moved from the extended position towards the retracted position. The rotator 29 is configured to translate linear movement of the delivery member cover 17 to rotation. The rotator 29 has a guide structure 29*a* configured to cooperate with radially inwards extending pins of the legs 17*b* of the delivery member cover 17 such that when the delivery member cover 17 is moved towards the retracted position the pins move against cam surfaces of the guide structure 29*a*. This causes rotation of the rotator 29 from the first rotational position to the second rotational position. When the delivery member cover 17 reaches the retracted position, the inner recesses, or windows, of the inner surface of the rotator 29 align with the flexible arms 31*b* of the rear cap structure 31. The flexible arms 31*b* are thereby able to flex radially outwards and disengage from the radial recesses 21*a* of the plunger rod 21 and the plunger rod 21 is thus released to move axially from the initial axial position towards the final position.

When the plunger rod 21 is released and reaches its final position, the U-shaped bracket 25 which previously was in engagement with the rear cap structure 31 is released and impacts with a radial surface, e.g., inside the rear cap structure 31. This causes an audible click, indicating that the medicament delivery operation has been finalised.

The medicament container 19, the cap 5, and in some examples, the housing 3, form or form part of the aforementioned sub-assembly of the medicament delivery device 1.

Figure 3:
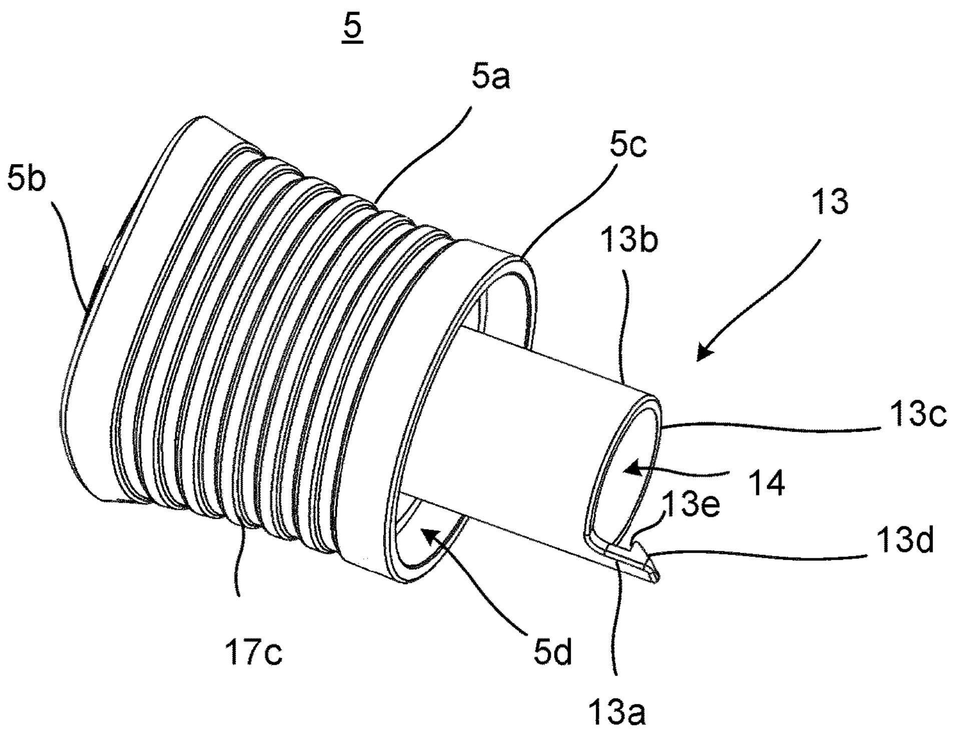
FIG. 3 depicts an example of the cap.

FIG. 3 shows a perspective view an example of the cap 5. The cap 5 has an outer cap body 5*a*. The outer cap body 5*a* has a proximal outer cap body end 5*b* and a distal outer cap body end 5*c*.

The needle shield remover 13 has a tubular inner cap body 13*b*. The gripping arm 13*a* extends axially in the distal direction from a distal tubular inner cap body end 13*c* of the tubular inner cap body 13*b*.

The tubular inner cap body 13*b* is arranged concentrically with the outer cap body 5*a*. The tubular inner cap body 13*b* is arranged radially inwards of the outer cap body 5*a*.

The tubular inner cap body 13*b* extends axially beyond the distal outer cap body end 5*c*. The gripping arm 13*a* thus also extend beyond the distal outer cap body end 5*c*.

A radial space 5*d* is formed between the tubular inner cap body 13*b* and the outer cap body 5*a*. The radial distance between the tubular inner cap body 13*b* and the outer cap body 5*a* is dimensioned such that at least a portion of the proximal tubular portion 17*a* of the delivery member cover 17 can be received in the radial space 5*d*.

The tubular inner cap body 13*b* defines a central channel 14 configured to receive the needle shield 8, e.g., the RNS 11 and/or the FNS 9.

The central channel 14 may be dimensioned to receive the needle shield 8 tightly or with a tight fit. The outer surface of the needle shield 8 may be in direct contact with the inner surface that forms the central channel 14. The outer surface of the needle shield 8 may be in direct contact with the inner surface that forms the central channel 14 around the entire perimeter of the needle shield 8.

The central channel 14 may be dimensioned to accommodate a majority of the axial length of the needle shield 8, for example at least 70% or 80% of the axial length of the needle shield 8.

According to the present example the cap 5 comprises a single gripping arm 13*a*.

The gripping arm 13*a* comprises a radially inwards extending structure 13*d*. The radially inwards extending structure 13*d* may have a radial dimension that decreases gradually in a direction towards a distal end face of the gripping arm 13*a*. The radially inwards extending structure 13*d* may for example have a wedge or ramp shape with an increasing radial dimension in a direction towards the proximal outer cap body end 5*b*.

The radially inwards extending structure 13*d* has a proximally directed radial surface 13*e* configured to bear against the distal end face of the needle shield 8, e.g., the distal end face 11*a* of the RNS 11 and/or the distal end face 9*a* of the FNS 9 when the cap 5 is removed.

Figure 4:
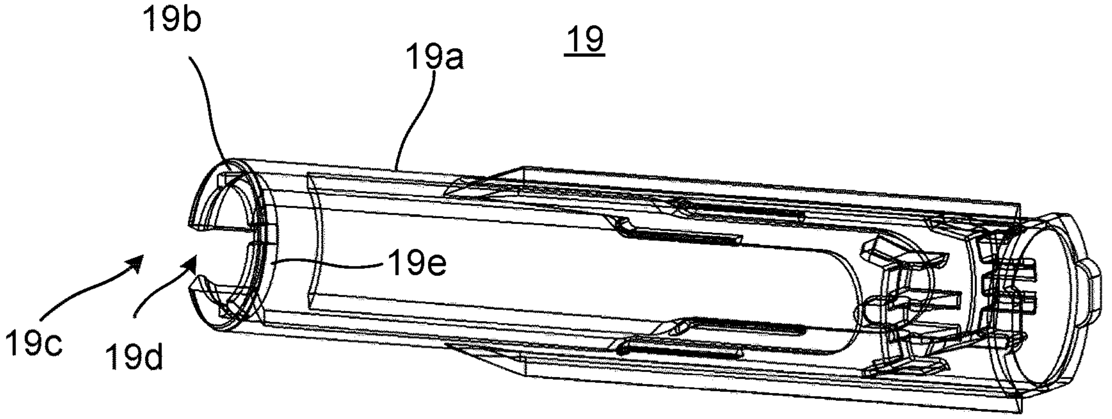
FIG. 4 shows a perspective view of the medicament container holder.

FIG. 4 shows a perspective view of the medicament container holder 19. The medicament container holder 19 comprises a holding body 19*a*. The holding body 19*a* is configured to receive or accommodate the medicament container 7.

The holding body 19*a* has a proximal holding body end 19*b*. The proximal holding body end 19*b* has a c-clip structure 19*c*. The c-clip structure 19*c* has radially flexible open ends in the circumferential direction of the holding body 19*a*. An axial slot 19*d* is formed between the open ends. The axial slot 19*d* is dimensioned to receive the gripping arm 13*a* when the cap 5 is fitted to the delivery member cover 17.

The c-clip structure 19*c* has a radially inwards extending ledge 19*e*. The ledge 19*e* is configured to support a shoulder of the medicament container 7. The shoulder may be a proximal portion of the medicament container in a region where its radial dimension decreases.

Figure 5:
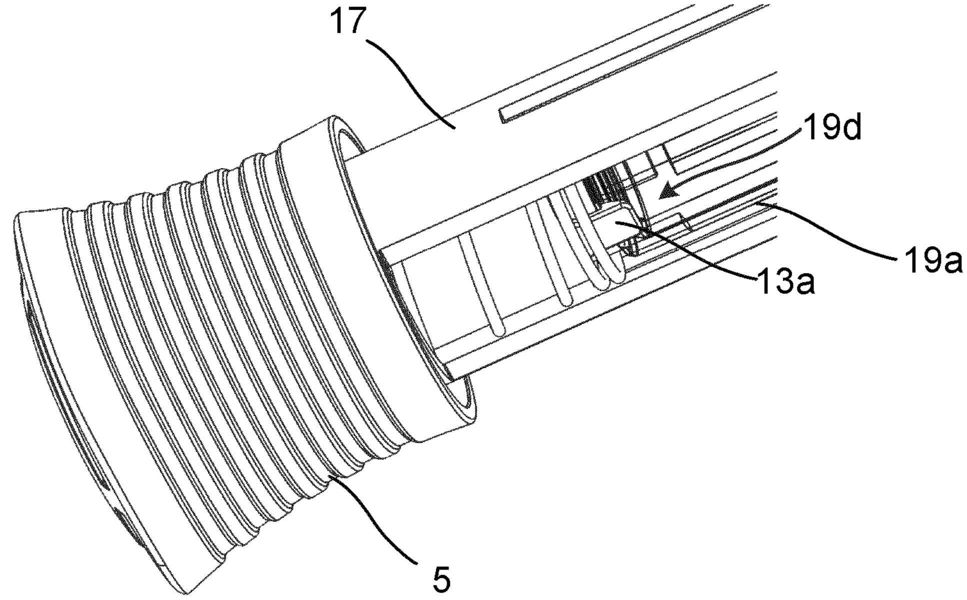
FIG. 5 is a perspective view of a proximal portion of the medicament delivery device with the cap fitted and the housing removed.

FIG. 5 shows the medicament delivery device 1 with the housing 3 removed before the cap 5 has been removed. The cap 5 is fitted to the delivery member cover 17 and receives a portion of the needle shield 8. The gripping arm 13*a* is arranged in the axial slot 19*d* of the holding body 19*a*. The gripping arm 13*a* is arranged to grip the needle shield 8 when the cap 5 is removed from the delivery member cover 17.

Figure 6:
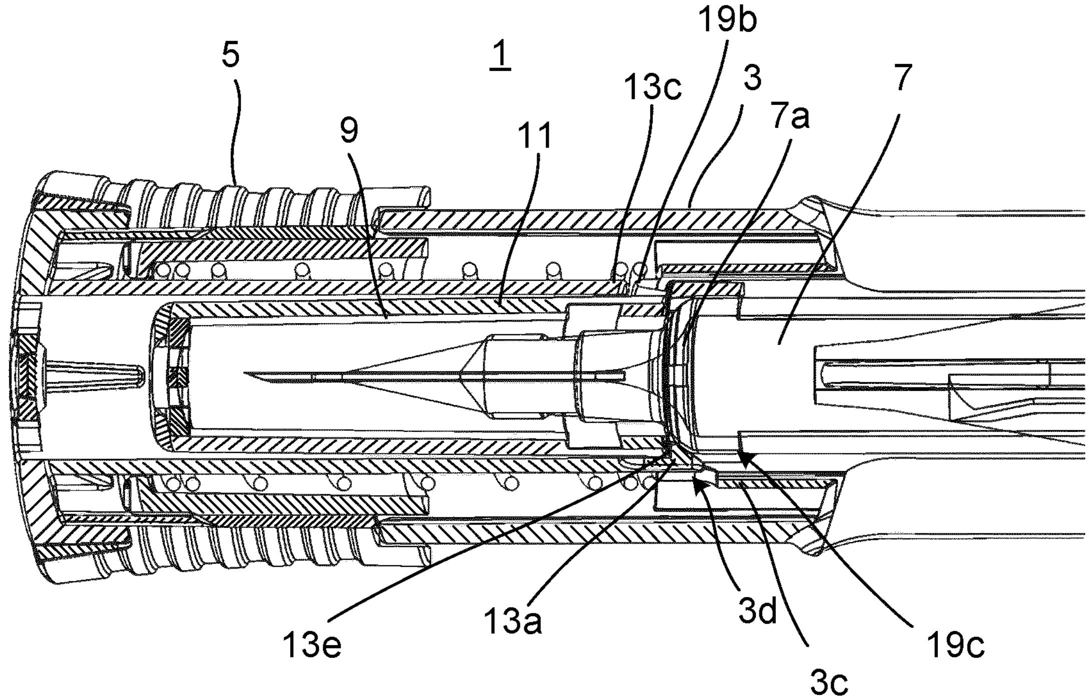

FIG. 6 shows the medicament delivery device 1 including the housing 3, before the cap 5 has been removed in a longitudinal section.

The medicament container 7 is arranged in the housing 3. The shoulder 7*a* bears against the ledge 19*e* of the medicament container holder 19.

The distal tubular inner cap body end 13*c* is arranged adjacent to the proximal holding body end 19*b* of the medicament container holder 19. In another example, the distal tubular inner cap body end 13*c* extends axially almost up to the proximal holding body end 19*b*. The axial distance between the distal tubular inner cap body end 13*c* and the proximal holding body end 19*b* is less than the axial extension of the gripping arm 13*a* from the distal tubular inner cap body end 13*c*.

The housing 3 has an inner wall 3*c* arranged axially aligned with the c-clip structure 19*c*. The inner wall 3*c* is thus axially arranged in level with the c-clip structure 19*c*. The inner wall 3*c* is arranged radially outwards of the c-clip structure 19*c*. The inner wall 3*c* is configured to restrict radial outward flexing of the c-clip structure 19*c*. Thereby, the radially inwards extending ledge 19*e* can prevent the medicament container 7 from moving in the proximal direction relative to the housing 3. Furthermore, during the assembling process of the medicament delivery device, the inner wall 3*c* is arranged radially so close to the outer surface of the c-clip structure 19*c* that the c-clip structure 19*c* is restricted to flex radially outward.

The inner wall 3*c* has an axial inner wall slot 3*d* configured to receive the gripping arm 13*a*. The gripping arm 13*a* is arranged in the axial slot 19*d* and in the axial inner wall slot 3*d* simultaneously when the cap 5 is mounted around the delivery member cover 17. A radial outer portion of the gripping arm 13*a* extends into the axial inner wall slot 3*d* and a radial inner portion of the gripping arm 13*a* extends into the axial slot 19*d* of the holding body 19*a*.

During assembly, the medicament container 7 may already be placed in the medicament delivery device 1 when the cap 5 is being fitted. The gripping arm 13*a* may thus slide into the axial slot 19*d* and the axial inner wall slot 3*d* when the cap 5 is placed over the delivery member cover 17 and the needle shield 8. The cap 5 is pushed in a direction against the housing 3 until the gripping arm 13*a* obtains a position in which the proximally directed radial surface 13*e* is arranged distally relative to the distal end face of the needle shield 8. Alternatively, during assembly, the cap may already be placed over the delivery member cover and attached to the proximal end of the housing. In this example, the medicament container holder will first be held at a distal position, e.g. by an assembling tool or an engagement with the housing. The medicament container with the needle shield will then be inserted into the medicament container holder from the distal end of the housing and the distal end of the medicament container holder. During the insertion of the medicament container into the medicament container holder, the needle shield flexes the c-clip radially outward when the needle shield passes through the proximal end of the medicament container holder. The c-clip then flexes radially inward once the needle shield moves past the proximal end of the medicament container holder. The medicament container holder and the medicament container then move together in the proximal direction relative to the housing towards the cap to a proximal position where the inner wall of the housing restricts the c-clip from flexing radially outward. Further proximal movement of the medicament container holder with the medicament container results in that the needle shield moves into the needle shield remover of the cap. The gripping arm may thus position into the axial slot when the needle shield enters into the needle shield remover.

Thus, after assembly but before removal of the cap 5, the proximally directed radial surface 13*e* of the radially inwards extending structure 13*d* is arranged distally relative to the distal end face of the needle shield 8, in this example the distal end face 9*a*, 11*a*, of both the FNS 9 and the FNS 11. The proximally directed radial surface 13*e* extends radially inwards so that it engages with or bears against the distal end face of the needle shield 8, i.e., in this example of both the FNS 9 and the FNS 11, when the cap 5 is pulled off the delivery member cover 17.

Figure 7:
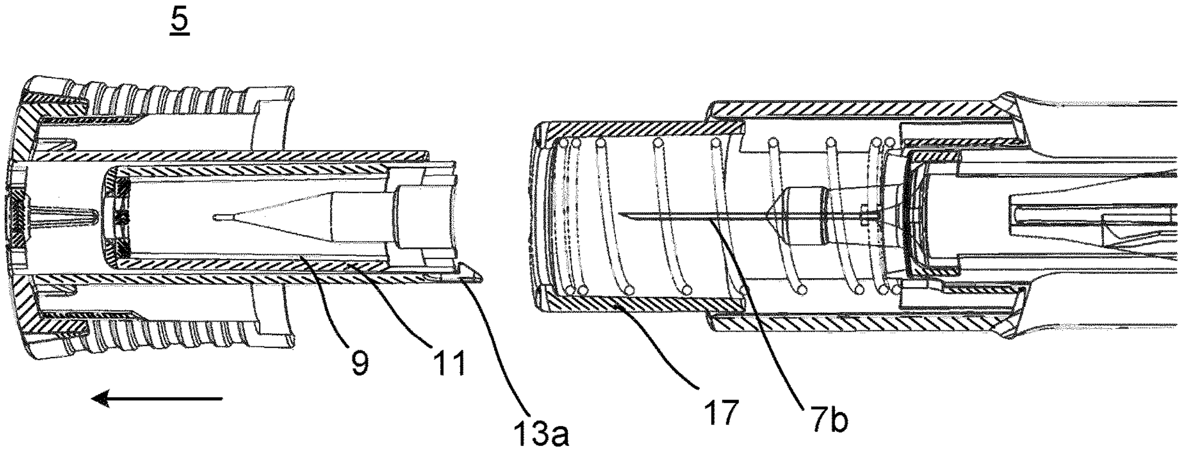
FIG. 7 is a longitudinal section of the medicament delivery device after the cap has been removed.

FIG. 7 depicts when the cap 5 has been pulled off from the delivery member cover 17. The gripping arm 13*a* engages with the distal end face of the needle shield 8, in this example comprising both the FNS 9 and the FNS 11. Thus, the needle shield is removed together with the cap 5. The delivery member 7*b*, a needle, is thus exposed inside the delivery member cover 17.

When the medicament delivery device 1 is pressed against a site of injection the delivery member cover 17 is moved towards the retracted position, triggering medicament delivery.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A sub-assembly for a medicament delivery device, comprising:

a cap comprising:

an outer cap body, a needle shield remover having a tubular inner cap body arranged concentrically with and radially inwards of the outer cap body, the tubular inner cap body defining a central channel configured to receive a needle shield, the needle shield remover comprising a gripping arm extending axially in a distal direction from a distal tubular inner cap body end of the tubular inner cap body; and a medicament container comprising:

a holding body configured to receive a medicament container, the holding body having a proximal holding body end provided with a c-clip structure, the c-clip structure having open ends in the circumferential direction of the holding body, whereby an axial slot is formed between the open ends, wherein the c-clip structure has a radially inwards extending ledge configured to axially support a shoulder of the medicament container, and wherein the gripping arm is configured to be arranged in the slot and engage with a distal end face of the needle shield.

2. The sub-assembly as claimed in claim 1, wherein the outer cap body has a distal outer cap body end, and wherein the tubular inner cap body extends distally beyond the distal outer cap body end.

3. The sub-assembly as claimed in claim 1, wherein the gripping arm comprises a radially inwards extending structure provided with a proximally directed radial surface configured to bear against the distal end face of the needle shield.

4. The sub-assembly as claimed in claim 3, wherein the radially inwards extending structure has a gradually decreasing radial dimension in a direction towards a distal end face of the gripping arm.

5. The sub-assembly as claimed in claim 1, wherein the cap is made of plastic.

6. The sub-assembly as claimed in claim 1, wherein the central channel is dimensioned to tightly fit the needle shield.

7. The sub-assembly as claimed in claim 1, wherein the central channel is dimensioned to accommodate a majority of the length of the needle shield.

8. The sub-assembly as claimed in claim 1, wherein the central channel is dimensioned to accommodate at least 70% to 80% of the length of the needle shield.

9. The sub-assembly as claimed in claim 1, wherein the distal tubular inner cap body end is arranged adjacent to the proximal holding body end.

10. The sub-assembly as claimed in claim 1, wherein the needle shield remover comprises only one gripping arm.

11. The sub-assembly as claimed in claim 1, wherein the needle shield comprises a rigid needle shield and/or a flexible needle shield.

12. The sub-assembly as claimed in claim 1, comprising a housing, wherein the housing is configured to receive the medicament container holder, wherein the housing has an inner wall arranged axially aligned with the c-clip structure, the inner wall being configured to restrict radial outward flexing of the c-clip structure.

13. The sub-assembly as claimed in claim 12, wherein the inner wall comprises an axial inner wall slot configured to receive the gripping arm.

14. A medicament delivery device comprising the sub-assembly of claim 1.

* * * * *